United States Patent [19]

Li

[11] Patent Number: 5,565,201
[45] Date of Patent: Oct. 15, 1996

[54] PHARMACEUTICAL COMPOSITION AND PREPARATION FOR THE TREATMENT OF SNORING AND THE USE THEREOF

[76] Inventor: Hongzhi Li, No.91, 11 Building, Xincun Erli Fengtai District, Beijing, China

[21] Appl. No.: 426,912

[22] Filed: Apr. 21, 1995

[30] Foreign Application Priority Data

Feb. 25, 1995 [CN] China ............................. 95 1 00029.2

[51] Int. Cl.⁶ .................................................. A61K 35/78
[52] U.S. Cl. ....................................... 424/195.1; 514/923
[58] Field of Search ........................... 424/195.1; 514/923

[56] References Cited

U.S. PATENT DOCUMENTS 5,225,203  7/1993  Kim ...................................... 424/195.1

*Primary Examiner*—John W. Rollins
*Attorney, Agent, or Firm*—Sughrue, Mion, Zinn, Macpeak & Seas

[57] ABSTRACT

The present invention relates to a novel composition for the treatment and inhibitation of snoring. The composition according to the present invention comprises a first component and a second component. The first component is selected from *Rhizoma dioscoreae nipponicae* and *Zingiber officinale*, and the second component comprises one of more plants selected from *Zingiber officinale* and the Dioscoreaceae, wherein the first component is different from the second component. The present invention further involves a preparation made by the anti-snoring composition of the present invention.

16 Claims, 2 Drawing Sheets

PHARMACEUTICAL COMPOSITION AND PREPARATION FOR THE TREATMENT OF SNORING AND THE USE THEREOF

FIELD OF THE INVENTION

The present invention relates to a novel pharmaceutical composition for the treatment of snoring and a therapeutic method of snoring.

BACKGROUND OF THE INVENTION

Snoring, also be named as syndrome of respiratory suspension in sleep, is a common phenomenon in sleep. The occurrence of snoring is caused by the relax of muscles in the muscle group of the upper respiratory tract, making the upper respiratory tract relatively narrow and the effective ventilation level of pharyngeal cavity decreased. During the sleeping, respiratory air flow passes through the narrow pharyngeal portion, and initiates the vibration of uvulae and the fringe of palatum molle on account of the increasing resistance, so that snoring occurs. Among the middle aged and old people, the occurrence rate of snoring is about 25%~35%. The snoring not only annoys the sleep and rest of the family and others around, but also does harm to the health of the snorer. To the severe snorer, the respiration stops 60~80 times per hour, and 10~30 seconds for each time, which can make air exchange in the lung decrease and the oxygen in blood inadequate, so that hypoxemia, hypercapnia and cardio-cerebral diseases will be caused.

For many years, people have been seeking for the method for the treatment of snoring. A mechanical device was once applied to expand the nostril by inserting the device into nose in an attempt of solving the problem of snoring. However, it is quite obvious that the use of mechanical device makes people feel uncomfortable and it is not very effective. Surgical operation has also been applied to treat snoring. However, in the practice, the surgical operation not only costs highly, but also can not be easily accepted by many patients of snoring. As a result, there are only a few people who adopt the surgical operation Obviously, it is highly desired to develop an effective and readily acceptable method to solve the snoring problem.

The present inventor has been devoting to research on the method for treating snoring for many years. The present inventor believes that gas flow can be passed smoothly by the expansion of the effective ventilation area of pharyngeal cavity, and the aim of treating snoring can thus be achieved. The expansion of the effective ventilation area of pharyngeal cavity can be made by:regulating the functions of lung, spleen and kidney, and strengthening the muscular tension of the upper respiratory tract. The present inventor has found in the studies that the coordination of *Rhizoma dioscoreae nipponicae* and *Zingiber officinale* etc. can expand the pharyngeal cavity to make the gas flow pass smoothly and to achieve the aim of reducing or inhibiting snoring.

One object of the present invention is to provide a composition for the treatment of snoring.

Another object of the present invention is to provide a preparation for the inhibition of snoring.

Further object of the present invention is to provide a new method of the treatment of snoring.

SUMMARY OF THE INVENTION

The present invention relates to a pharmaceutical composition for the treatment of snoring. The said composition comprises first component which is one element selected from a group consisting of *Rhizoma dioscoreae nipponicae* and *Zingiber officinale* and second component which is one or more elements selected from a group consisting of *Zingiber officinale* and Dioscoreaceae, wherein the first component is different from the second component. Preferably, the said composition includes *Rhizoma dioscoreae nipponicae* and *Zingiber officinale*.

The present invention further relates to a method for the treatment of snoring. The said method is to administrate the anti-snoring composition according to the present invention in an effective amount to nasal cavity and/or nasal portion of a patient The present invention further provides a preparation for the treatment of snoring. The said preparation comprises an effective amount of the said composition and physiologically acceptable carriers and/or excipients.

THE BRIEF DESCRIPTION OF THE DRAWINGS

DETAILED DESCRIPTION OF THE INVENTION

Figure 1:
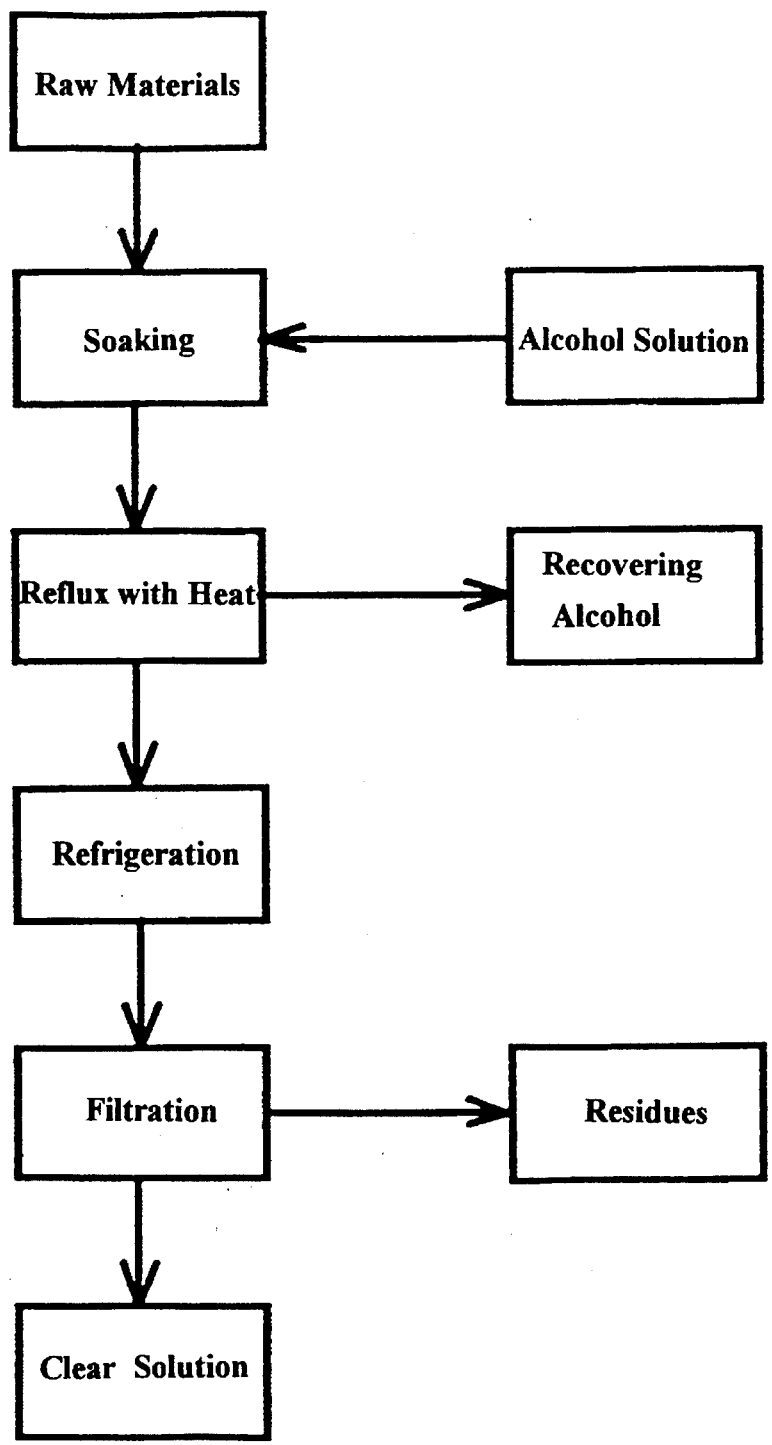
FIG. 1 is a flow chart of preparing the anti-snoring composition of the present invention.

According to the present invention, a composition for the treatment of snoring comprises first component which is one element selected from a group consisting of *Rhizoma dioscoreae nipponicae* and *Zingiber officinale* and second component which is one or more elements selected from a group consisting of *Zingiber officinale* and Dioscoreaceae, wherein the first component is different from the second component. In the present description and claims, the term of Dioscoreaceae does not include *Rhizoma dioscoreae nipponicae*.

According to the present invention, a composition for the treatment of snoring comprises *Rhizoma dioscoreae nipponicae* and one or more plants selected from the ioscoreaceae. The *Rhizoma dioscoreae nipponicae* in the said composition is not less than about 40% by weight. The said plant of the Dioscoreaceae is preferably *Rhizoma dioscoreae*.

A composition for the treatment of snoring comprises *Zingiber officinale* and one or more plants selected from the Dioscoreaceae. In the said composition, *Zingiber officinale* is about 10~30% by weight, the plant(s) of the Dioscoreaceae is about 70~90% by weight.

A composition for the treatment of snoring comprises *Rhizoma dioscoreae nipponicae* and *Zingiber officinale*. In the said composition, *Rhizoma dioscoreae nipponicae* is about 50~90% by weight, and *Zingiber officinale* is about 10~50% by weight. The composition further comprises one or more plants selected from the Dioscoreaceae. In the composition, Rhizoma dioscoreae nipponicae is about 20~40% by weight, *Zingiber officinale* is about 10~20% by weight and the plant(s) of the Dioscoreaceae is about 40~70% by weight.

*Rhizoma dioscoreae nipponicae*, *Zingiber officinale* and plants of the Dioscoreaceae are available in market, and their sources may be from either artificial cultivation or natural growth. In the present invention, the rhizome and/or stem tuber of *Rhizoma dioscoreae nipponicae*, *Zingiber officinale* and plants of the Dioscoreaceae are preferably used as raw materials. The Dioscoreaceae of the present invention includes various plants, e.g. *Dioscorea nipponica, Dioscorea opposita* Thunb, *Dioscorea althaeoides* R. Knuth, *Dioscorea tokoro* Makino, *Dioscorea zingiberensis* C. H. Wright, *Dioscorea parviflora* C. T. Ting, *Dioscorea deltoidea* Wall, *Dioscorea panthaica* Prain et Burkill, *Dioscorea biformifolia* Pei et C. T. Ting, *Dioscorea gracillima* Miq., *Dioscorea collettii* Hook. f., *Dioscorea futschauensis* Uline ex R. Knuth, *Dioscorea septemloba* Thunb., *Dioscorea tenuipes* Franch. et Sayat., *Dioscorea poilanei* Prain et Burkill, *Dioscorea chingii* Prain et Burkill, *Dioscorea banzuana* Pei et C. T. Ting, *Dioscorea simulans* Prain et Burkill, *Dioscorea bulbifera* L., *Dioscorea yunnanensis* Prain et Burkill, *Dioscorea henryi* (Prain et Burkill) C. T. Ting, *Dioscorea japonica* Thunb.

According to the present invention, a preparation for the treatment of snoring comprises an effective amount of anti-snoring composition and a physiologically acceptable carrier and/or excipient, wherein the said composition comprises first component which is one element selected from a group consisting of *Rhizoma dioscoreae nipponicae* and *Zingiber officinale*, and second component which is one or more element selected from a group consisting of *Zingiber officinale* and Dioscoreaceae, wherein the first component is different from the second component.

A preparation for the treatment of snoring comprises an effective amount of anti-snoring composition and a physiologically acceptable carrier and/or excipient, wherein the said composition comprises *Rhizoma dioscoreae nipponicae* and one or more plants selected from the Dioscoreaceae. In the composition, the content of *Rhizoma dioscoreae nipponicae* is not less than 40% by weight.

A preparation for the treatment of snoring comprises an effective amount of anti-snoring composition and a physiologically acceptable carrier and/or excipient, wherein the said composition comprises *Zingiber officinale* and one or more plants of selected from the Dioscoreaceae. In the composition, the content of *Rhizoma dioscoreae nipponicae* is not less than 40% by weight A preparation for the treatment of snoring comprises an effective amount of anti-snoring composition and a physiologically acceptable carrier and/or excipient, wherein the said composition comprises *Zingiber officinale* and one or more plants selected from the Dioscoreaceae. In the composition, the content of *Zingiber officinale* is about 10~30% by weight, and the content of Dioscoreaceae plant(s) is about 20~90% by weight.

A preparation for the treatment of snoring comprises an effective amount of anti-snoring composition and a physiologically acceptable carrier and/or excipient, wherein the said composition comprises *Rhizoma dioscoreae nipponicae* and *Zingiber officinale*. In the composition, the content of *Rhizoma dioscoreae nipponicae* is about 50~90% by weight; the content of *Zingiber officinale* is about 10~50% by weight. The said composition may further comprise one or more plants selected from the Dioscoreaceae.

The preparation of the present invention scan be formulated into various desired forms, such as: nasal drops, sprays, powder, suppositories, ointments, sticking membranes etc. The carriers and/or excepients used in the present invention are conventional and physiologically acceptable, which are well known to the person skilled in the arts. For example, they can be starch, gelatin, Stearic acid, geoline, octadecanol, glycerin, alcohol, sodium chloride or distilled water or their mixture etc.

The administration is usually taken through nasal cavity and/or nasal portion. The composition of the present invention is administrated at a dosage of 0.1 mg or more per kg of body weight of adult, which can be administrated before the sleep.

According to the present invention, a preparation for the treatment of snoring comprises: (by weight)

| | | |
|---|---|---|
| anti-snoring composition of the present invention | | 5~15% |
| alcohol | | 1~5% |
| glycerin | | 7~11% |
| sodium chloride | | 0.6~1.0% |
| distilled water | added to | 100% | wherein the anti-snoring composition of the present invention is preferably the composition which includes *Rhizoma dioscoreae nipponicae* and *Zingiber officinale*

According to the present invention, a method for the treatment of snoring comprise administrating an effective amount of the anti-snoring composition of the present invention.

A. ACUTE TOXICITY TEST 20 small mice (10 males and 10 females) were starved for 3~4 hours. Each mouse was administered by gavage with the composition of the present invention at a dosage of 1.0 ml (containing 49.5 mg of the composition per ml) for each time. After 7 days, abnormal actions such as slow action, bristling, sweating, anorexia, loss of body weight, or death were not found in the tested mice.

Thus, the result of the acute toxicity test shows that the $LD_{50}$ of the mice is over 50 ml/kg, who was orally administrated the composition of the present invention.

B. IRRITATING TEST OF NASAL MUCOSA

Take 20 SD rats, each weighting 200~300 g with male and female each in half. The rats were randomly divided into two groups. One group were dripped with the composition of the present invention in two drops/time/day, which contained 49.5 mg of the composition per mi. Another group were dripped with two drops of physiological saline once daily. Both of them were administrated daily for a week, then the rats were killed after 24 hours from the last administration. The local nasal mucoasa was taken and observed whether or not they had phenomena such as congestion and swelling etc. Neither congestion nor abnormal secretion from nasal mucosa of rats was seen macroscopically, which indicates that the composition of the present invention has no obvious irritative effect to nasal mucosa.

C. CLINICAL TEST

Clinical Information

I. Observed Recipients

There were 162 cases of patients in the test, in which male patients were 148 cases and female 14 cases, with male:female=10.6:1

II. The Ages of Recipient

The ages of recipients are ranged from 26 to 68, with 53 as average, described in table 1.

TABLE 1

Ages of Recipients

| Age | 30 or below | 31–40 | 41–50 | 51–60 | Over 60 | Total |
| --- | --- | --- | --- | --- | --- | --- |
| Cases | 18 | 36 | 36 | 54 | 18 | 162 |

The Method of Observation and Therapy

I. Therapy
1. Two to four drops of the anti-snoring preparation containing the composition of the present invention dripped into each nostril of the recipient before sleeping each night.
2. The course of treatment: There were two weeks per course of treatment, and the continued courses will be allowed if it is effective but uncurable.

II. The Method of Observation

Recorders were put aside the pillow of the recipients for the whole night to record their snoring status, who slep without administration of the anti-snoring medicine and with administration of the anti-snoring medicine of the present invention, so as to contrast the snoring status before and after the administration.

III. The Standard to Determine the Effect of the Therapy

Obviously effective: without snoring essentially;

Effective: snoring (including volume and frequency of the sound) obviously relieves and/or falls;

Non-effective: snoring remains unchanged essentially.

Results of the Observation

I. General conditions of the therapeutic effectiveness for the recipients are shown in Table 2.

TABLE 2

Evaluation for the Therapeutic Effectiveness of the 162 Snoring Cases

|  | Obviously effective | Effective | Non-effective | Total |
| --- | --- | --- | --- | --- |
| Persons | 18 | 139 | 5 | 162 |
| Rate (%) | 11.11 | 85.80 | 3.09 | 100 |

II. The relationship between the therapeutic effectiveness and sex is shown in Table 3.

TABLE 3

The Relationship between Therapeutic Effectiveness and Sex of the 162 Snoring Cases

|  | Male | Female | Total |
| --- | --- | --- | --- |
| Obviously effective | 14 | 4 | 18 |
| Effective | 130 | 9 | 139 |
| Non-effective | 4 | 1 | 5 |
| Total | 148 | 14 | 162 |

III. The relationship between therapeutic effectiveness and ages is shown in Table 4.

TABLE 4

The Relationship between Therapeutic Effectiveness and Ages of the 162 Snoring Cases

| Ages | Below 30 | 31–40 | 41–50 | 51–60 | Over 60 | Total |
| --- | --- | --- | --- | --- | --- | --- |
| Obviously effective | 2 | 5 | 5 | 4 | 2 | 18 |
| Effective | 16 | 30 | 30 | 49 | 14 | 139 |
| Non-effective | 0 | 1 | 1 | 1 | 2 | 5 |
| Total | 18 | 36 | 36 | 54 | 18 | 162 |

Many conventional methods may be used to prepare the anti-snoring composition of the present invention, such as extraction with boiling and precipitation with alcohol or extraction with reflux etc., which are well known to the skilled persons in the art. At the following, We take the method of the extraction with reflux as an example to illustrate the preparing process for the composition of the present invention.

Referring to FIG. 1, raw materials were soaked with alcohol aqueous solution for more than 8 hours. Hermetic container is preferably used for soaking to reduce the volatilization loss of alcohol. The alcohol aqueous solution was prepared by medical alcohol and distilled water available in market, and was in the content of about 20%~70%, preferable 55%~70%. The soaked mixture was heated to reflux for more than 5 hours. In the period of reflux, partial alcohol may be removed, and the removed alcohol can be recovered for further use. The refluxed mixture was refrigerated at 0°~4° C. for more than 24 hours. The refrigeration was preferably carried out in a hermetic container. The cooled mixture was filtered and then removed of residues so that the clear alcohol aqueous solution of the composition according to the present invention was obtained. The said solution may be prepared to form a 10% of tincture or be processed to form a solid anti-snoring composition. According to the present invention, each component in the raw materials may be mixed before the above process to obtain the anti-snoring composition. Each component may also be processed individually according to the above method, the alcohol aqueous solution or powder of each component which is individually processed was then mixed in certain proportion to give the anti-snoring composition of the present invention, or alcohol aqueous solution (tincture) or powder of these individual components can be directly used to formulate a preparation.

Conventional methods can be applied to formulate the anti-snoring preparation of the present invention, which are well known to the skilled person in the art. Common physiologically acceptable carriers and/or excipients were used in the preparation, such as glycerin, sodium chloride etc. The preparation can be formulated by the anti-snoring composition of the present invention or by each individually processed component in the form of tincture or powder in the certain proportion according to the present invention.

Figure 2:
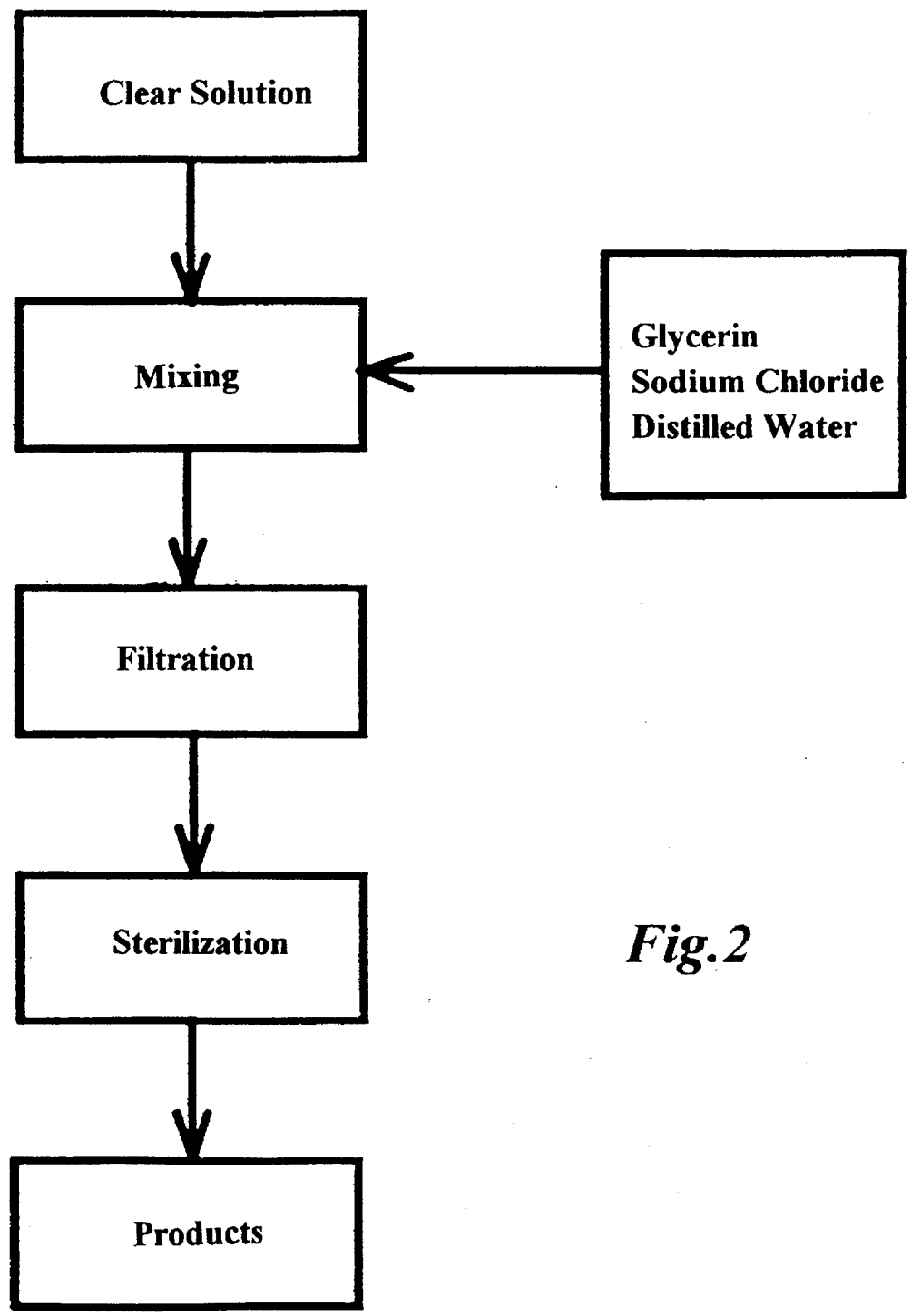
FIG. 2 is a flow chart of preparing the anti,snoring preparation of the present invention

The clear alcohol aqueous solution of the anti-snoring composition according to the present invention is used as an example to illustrate the process of the preparation of the present invention. Referring to FIG. 2, the clear alcohol aqueous solution of the anti-snoring composition of the present invention was mixed with glycerin, sodium chloride and distilled water. The mixture was then filtered and sterilized, and thus to obtain the anti-snoring preparation of the present invention. Common devices and methods were used to filtration and sterilization.

The present invention is further illustrated by the following examples, but which by no means limit the scope of the present invention.

EXAMPLE 1

800 g of *Rhizoma dioscoreae nipponicae* and 200 g of *Zingiber officinale* were taken to be crushed or sliced respectively. 10 times of distilled water was added. And they were soaked in hermetic container at room temperature for 12 hours. Then the mixture was heated and extracted with boiling for 6 hours. After the mixture was filtered, 5% of alcohol was added. The mixture was then cooled and kept at 0°~4° C. for 48 hours, and filtered. Thus a clear alcohol aqueous solution of the anti-snoring composition was obtained.

EXAMPLE 2

500 g of each *Rhizoma dioscoreae nipponicae* and *Zingiber officinale* were taken to be crushed or sliced. 10 times of 60% of alcohol aqueous solution was added and soaked for 48 hours. Then the mixture was heated and extracted with reflux. During the reflux, partial alcohol was recovered after the mixture was boiled for 0.5 hours. The mixture was cooled at 0°~4° C. for 36 hours and then filtered to obtain a clear alcohol aqueous solution of the anti-snoring composition. After being concentrated and dried, the powder form of the anti-snoring composition of the present invention was obtained.

EXAMPLE 3

According to the method of Example 1, a product was produced by starting from 300 g of *Rhizoma dioscoreae nipponicae*, 200 g of *Zingiber officinale* and 500 g of *Dioscorea opposita* Thunb.

EXAMPLE 4

According to the method of Example 2, a product was produced by starting from 300 g of *Rhizoma dioscoreae nipponicae*, 100 g of *Zingiber officinale*, 300 g of *Dioscorea opposita* Thunb and 300 g of *Dioscorea deltoidea* Wall.

EXAMPLE 5

According to the method of Example 1, a product was produced by starting from 500 g of *Rhizoma dioscoreae nipponicae*, 300 g of *Dioscorea opposita* Thunb and 200 g of *Dioscorea septemloba* Thunb.

EXAMPLE 6

According to the method of Example 1, a product was produced by starting from 100 g of *Zingiber officinale*, 500 g of *Dioscorea opposita* Thunb and 400 g of *Dioscorea hemsleyi* Prain et Burkill.

EXAMPLE 7

According to the method of Example 1, a product was produced by starting from 400 g of *Rhizoma dioscoreae nipponicae* and 600 g of *Dioscorea opposita* Thunb.

EXAMPLE 8

According to the method of Example 2, a product was produced by starting from 200 g of *Zingiber officinale* and 800 g of *Dioscorea septemloba* Thunb.

EXAMPLE 9

Taking 5 L of 10% of *Rhizoma dioscoreae nipponicae* tincture and 5 L of 10% of *Zingiber officinale* tincture, 10 L of glycerin and 0.9kg of sodium chloride were added, and distilled water was added to 100 L. The mixture was stirred to be mixed evenly, and then filtered and sterilized. Thus an anti-snoring preparation was obtained.

What is claimed is:

1. A composition for the treatment of snoring, comprising a first component and a second component, wherein the first component is present in an amount effective to reduce or inhibit snoring and is an extract of a material selected from the group consisting of *Rhizoma dioscoreae nipponicae* and *Zingiber officinale*, and the second component is present in an amount effective to reduce or inhibit snoring and is an extract of a material selected from the group consisting of *Zingiber officinale* and Dioscoreaceae, wherein the first component is different from the second component.

2. A composition for the treatment of snoring according to claim 1, wherein the first component is an extract of *Rhizoma dioscoreae nipponicae*, the second component is an extract of a plant of the Dioscoreaceae, and the amount of the extract of the *Rhizoma dioscoreae nipponicae* in the composition is at least 40% by weight.

3. A composition for the treatment of snoring according to claim 1, wherein the first component is an extract of *Zingiber officinale*, the second component is an extract of a plant of the Dioscoreaceae, and in the composition the extract of the *Zingiber officinale* is about 10–30% by weight and the extract of the plant of the Dioscoreaceae is about 70–90% by weight.

4. A composition for the treatment of snoring according to claim 1, wherein the first component is an extract of the *Rhizoma dioscoreae nipponicae*, the second component is an extract of *Zingiber officinale*, and in the composition the extract of the *Rhizoma dioscoreae nipponicae* is about 50–90% by weight and the extract of the *Zingiber officinale* is about 10–50% by weight.

5. A composition for the treatment of snoring according to claim 1, wherein the first component is an extract of *Rhizoma dioscoreae nipponicae*, the second component comprises an extract of *Zingiber officinale* and an extract of a plant of the Dioscoreaceae, and in the composition the extract of the *Rhizoma dioscoreae nipponicae* is about 20–40% by weight, the extract of the *Zingiber officinale* is about 10–20% by weight and the extract of the plant of the Dioscoreaceae is about 40–70% by weight.

6. A composition for the treatment of snoring according to claim 1, wherein the Dioscoreaceae is an extract of a plant of Dioscoreaceae selected from the group consisting of: *Dioscorea nipponica*, *Dioscorea opposita* Thunb, *Dioscorea althaeoides* R. Knuth, *Dioscorea tokoro* Makino, *Dioscorea zingiberensis* C. H. Wright, *Dioscorea parviflora* C. T. Ting, *Dioscorea deltoidea* Wall, *Dioscorea panthaica* Prian et Burkill, *Dioscorea biformifolia* Pei et C. T. Ting, *Dioscorea gracillima* Miq., *Dioscorea collettii* Hook. f., *Dioscorea futschauensis* Uline ex R. Knuth, *Dioscorea septemloba* Thunb., *Dioscorea tenuipes* Franch et Savat., *Dioscorea poilanei* Prain et Burkill, *Dioscorea chingii* Prain et Burkill, *Dioscorea banzuana* Pei et C. T. Ting, *Dioscorea simulans* Prain et Burkill, *Dioscorea bulbifera* L., *Dioscorea yunnanensis* Prain et Burkill, *Dioscorea henryi* (Prain et Burkill) C. T. Ting, and *Dioscorea japonica* Thunb.

7. A preparation for the treatment of snoring, comprising an anti-snoring composition comprising a first component and a second component, wherein the first component is present in an amount effective to reduce or inhibit snoring and is an extract of a material selected from the group consisting of *Rhizoma dioscoreae nipponicae* and *Zingiber officinale*, and the second component is present in an amount effective to reduce or inhibit snoring and is an extract of a material selected from the group consisting of *Zingiber officinale* and Dioscoreaceae, wherein the first component is different from the second component, and a physiologically acceptable carrier.

8. A preparation for the treatment of snoring according to claim 7, wherein in the anti-snoring composition the *Rhizoma dioscoreae nipponicae* is about 50–90% by weight and the *Zingiber officinale* is about 10–15% by weight.

9. A composition for the treatment of snoring according to claim 7, further comprising an excipient.

10. A preparation for the treatment of snoring, comprising:

(a) an anti-snoring composition comprising an extract of *Rhizoma dioscorea nipponicea* and an extract of *Zingiber officinale*, the extract of *Rhizoma dioscorea nipponicea* comprising about 50–90% by weight of the composition and the extract of *Zingiber officinale* comprising about 10% by weight of the composition, the anti-snoring composition comprising about 5–15% by weight of the preparation;

(b) alcohol in an amount of about 1–5% by weight of the preparation;

(c) glycerin in an amount of about 7–11% by weight of the preparation;

(d) sodium chloride in an amount of about 0.6–1.0% by weight of the preparation; and (e) distilled water present in an amount to make 100% by weight of the preparation.

11. A method for the treatment of snoring, comprising the step of administering to a host in need thereof, an amount of an anti-snoring composition effective to reduce or inhibit snoring, the composition comprising a first component and a second component, wherein the first component is present in an amount effective to reduce or inhibit snoring and is an extract of a material selected from the group consisting of *Rhizoma dioscoreae nipponicae* and *Zingiber officinale*, and the second component is present in an amount effective to reduce or inhibit snoring and is an extract of a material selected from the group consisting of *Zingiber officinale* and Dioscoreaceae, wherein the first component is different from the second component.

12. A method for the treatment of snoring according to claim 11, wherein the first component is an extract of *Rhizoma dioscoreae nipponicae*, the second component is an extract of a plant of the Dioscoreaceae, and the amount of the extract of the *Rhizoma dioscoreae nipponicae* in the composition is at least 40% by weight.

13. A method for the treatment of snoring according to claim 11, wherein the first component is an extract of *Zingiber officinale*, the second component is an extract of a plant of the Dioscoreaceae, and in the composition the extract of the *Zingiber officinale* is about 10–30% by weight and the extract of the plant of the Dioscoreaceae is about 70–90% by weight.

14. A method for the treatment of snoring according to claim 11, wherein the first component is an extract of the *Rhizoma dioscoreae nipponicae*, the second component is an extract of *Zingiber officinale*, and in the composition the extract of the *Rhizoma dioscoreae nipponicae* is about 50–90% by weight and the extract of the *Zingiber officinale* is about 10–50% by weight.

15. A method for the treatment of snoring according to claim 11, wherein the first component is an extract of *Rhizoma dioscoreae nipponicae*, the second component comprises an extract of *Zingiber officinale* and an extract of a plant of the Dioscoreaceae, and in the composition the extract of the *Rhizoma dioscoreae nipponicae* is about 20–40% by weight, the extract of the *Zingiber officinale* is about 10–20% by weight and the extract of the plant of the Dioscoreaceae is about 40–70% by weight.

16. A method for the treatment of snoring according to claim 11, wherein the Dioscoreaceae is an extract of a plant of Dioscoreaceae selected from the group consisting of: *Dioscorea nipponica, Dioscorea opposita* Thunb, *Dioscorea althaeoides* R. Knuth, *Dioscorea tokoro* Makino, *Dioscorea zingiberensis* C. H. Wright, *Dioscorea parviflora* C. T. Ting, *Dioscorea deltoidea* Wall, *Dioscorea panthaica* Prian et Burkill, *Dioscorea biformifolia* Pei et C. T. Ting, *Dioscorea gracillima* Miq., *Dioscorea collettii* Hook. f., *Dioscorea futschauensis* Uline ex R. Knuth, *Dioscorea septemloba* Thunb., *Dioscorea tenuipes* Franch et Savat., *Dioscorea poilanei* Prain et Burkill, *Dioscorea chingii* Prain et Burkill, *Dioscorea banzuana* Pei et C. T. Ting, *Dioscorea simulans* Prain et Burkill, *Dioscorea bulbifera* L., *Dioscorea yunnanensis* Prain et Burkill, *Dioscorea henryi* (Prain et Burkill) C. T. Ting, and *Dioscorea japonica* Thunb.

* * * * *